United States Patent [19]

Appler

[11] Patent Number: 5,495,017
[45] Date of Patent: Feb. 27, 1996

[54] PREPARATION OF SUBSTANTIALLY DUST-FREE TETRAHYDRO-3,5-DIMETHYL-1,3,5-THIADIAZINE-2-THIONE GRANULES

[75] Inventor: Heinz Appler, Marktoberdorf-Balteratsried, Germany

[73] Assignee: BASF Aktiengesellschaft, Ludwigshafen, Germany

[21] Appl. No.: 244,742

[22] PCT Filed: Dec. 15, 1992

[86] PCT No.: PCT/EP92/02907

§ 371 Date: Jun. 13, 1994

§ 102(e) Date: Jun. 13, 1994

[87] PCT Pub. No.: WO93/13085

PCT Pub. Date: Jul. 8, 1993

[30] Foreign Application Priority Data

Dec. 21, 1991 [DE] Germany ............ 41 42 571.5

[51] Int. Cl.⁶ .................................. C07D 285/34
[52] U.S. Cl. ............................................ 544/8
[58] Field of Search .................................. 544/8

[56] References Cited

U.S. PATENT DOCUMENTS 2,838,389  6/1958  Yoder ........................................ 544/8

FOREIGN PATENT DOCUMENTS 1229662  3/1960  France .
1554038  12/1968  France .

OTHER PUBLICATIONS

Chem Asbstr. 166783g, vol. 102 (1985).

*Primary Examiner*—John M. Ford
*Attorney, Agent, or Firm*—Keil & Weinkauf

[57] ABSTRACT

Substantially dust-free granules of tetrahydro-3,5-dimethyl-1,3,5-thiadiazine-2-thione (I) are prepared by reacting methylamine (II) with carbon disulfide (III) and formaldehyde (IV) or by reacting the methylammonium salt of N-methyldithiocarbamic acid (V) with formaldehyde (IV) by a process in which the reaction is carried out in the presence of at least one diaminoalkylene of the formula VI $$R^1\text{-NH-A-NH-}R^2 \qquad \qquad \text{VI}$$

where $R^1$ and $R^2$ independently of one another are each hydrogen or alkyl and A is an unsubstituted or substituted 1,2-ethylene, 1,3-propylene or 1,4-butylene bridge.

10 Claims, No Drawings

PREPARATION OF SUBSTANTIALLY DUST-FREE TETRAHYDRO-3,5-DIMETHYL-1,3,5-THIADIAZINE-2-THIONE GRANULES

This application is a continuation of PCT/EP92/02907 filed Dec. 15, 1992.

The present invention relates to a process for the preparation of substantially dust-free granules of tetrahydro-3,5-dimethyl-1,3,5-thiadiazine-2-thione (I) by reacting methylamine (II) with carbon disulfide (III) and formaldehyde (IV) or by reacting the methylammonium salt of N-methyldithiocarbamic acid (V) with formaldehyde (IV).

The invention also relates to substantially dust-free granules of tetrahydro-3,5-dimethyl-1,3,5-thiadiazine-2-thione and to methods of soil decontamination and of controlling nematodes, germinating plants and soil fungi using these granules.

Tetrahydro-3,5-dimethyl-1,3,5-thiadiazine-2-thione (I) (common name: dazomet) is used in agriculture and horticulture for soil decontamination (against nematodes, germinating plants and soil fungi) (U.S. Pat. No. 2,838,389).

In the known preparation processes, the active ingredient is obtained in the form of a fine powder which furthermore has a high content of active ingredient as dust. Such a product is not suitable for the safe use of the active ingredient, which releases methyl isothiocyanate on decomposition.

The literature discloses that thiadiazine derivatives, such as tetrahydro-3,5-dimethyl-1,3,5-thiadiazine-2-thione (I), are obtained in the form of granules if the reaction of the starting materials is carried out in the presence of an emulsifier (Emulgen PP150) and zinc sulfate (JP-A 84/210 073=Chemical Abstracts 102 (19), 166 783 g). The granules thus prepared contain 10% of particles having a diameter of from 200 to 300 μm, 79% of particles having a diameter of from 100 to 200 μm and 11% of particles having a diameter of less than 100 μm.

However, problems with the disposal of the aqueous mother liquors may occur in this process, owing to the use of the inorganic salt and of the emulsifier.

It is an object of the present invention to provide a simpler process for the preparation of tetrahydro-3,5-dimethyl-1,3,5-thiadiazine-2-thione (I) in the form of granules.

We have found that this object is achieved by a process for the preparation of substantially dust-free granules of tetrahydro-3,5-dimethyl1,3,5-thiadiazine-2-thione (I) by reacting methylamine (II) with carbon disulfide (III) and formaldehyde (IV) or by reacting the methylammonium salt of N-methyldithiocarbamic acid (V) with formaldehyde (IV), wherein the reaction is carried out in the presence of at least one diaminoalkylene of the formula VI $$R^1\text{-NH-A-NH-}R^2 \qquad \text{VI}$$

where $R^1$ and $R^2$ independently of one another are each hydrogen or $C_1$–$C_4$-alkyl and A is a 1,2-ethylene, 1,3-propylene or 1,4-butylene bridge and these bridges may carry from one to four $C_1$–$C_4$-alkyl groups.

The reaction is carried out according to the following reaction scheme:

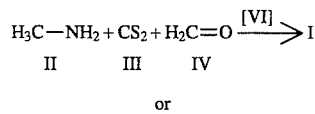

or

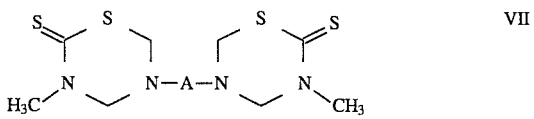

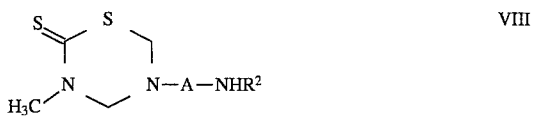

The process may be based on the fact that small amounts of the diaminoalkylene compound compete with methylamine in the reaction and, if $R^1$ and $R^2$ are simultaneously hydrogen, for example "dimers" of the formula VII or higher "polymers" of the active ingredient may thus be formed.

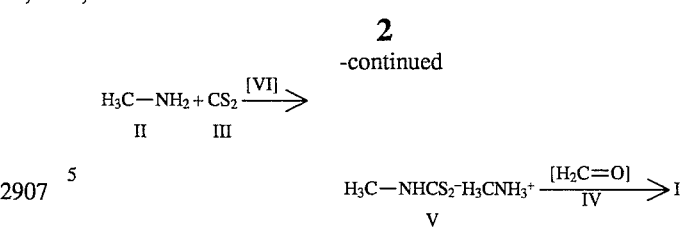

The diaminoalkylene compounds in which $R^1$ or $R^2$ is not hydrogen my result in the formation of, for example, byproducts of the following structure VIII.

Diaminoalkylene compounds in which neither $R^1$ nor $R^2$ is hydrogen might react with carbon disulfide to give non-cyclized products of the structure IX.

$$R^1\text{-}N^+H_2\text{-A-}NR^2\text{-}CS_2 \qquad \text{IX}$$

In addition to the possible byproducts described above, other structures are also possible.

However, the fact that the possible byproducts as well as the active ingredient itself are capable of releasing methyl isothiocyanate is of considerable importance. Consequently, the byproducts too could contribute to the activity in the granules.

The formation of the desired granules my be due to the fact that, on the one hand, byproducts of the structures assumed above are sufficient to disturb the "orderly" crystallization but, on the other hand, such compounds have sufficient similarity to the active ingredient itself, so that they form a disordered conglomerate with the crystals and hence the desired granules.

The novel process is usually carried out in aqueous solution, either in a one-stage synthesis or in two stages.

In the one-stage reaction, in general carbon disulfite is first added to an aqueous solution of methylamine and diaminoalkylene and an aqueous formaldehyde solution is then added (similarly to the process described in U.S. Pat. No. 2,838,389, column 6, lines 46–57).

In the reaction in two stages, in general carbon disulfide is first added to an aqueous solution of methylamine and diaminoalkylene, the solution of the resulting carbamate V is then freed from excess carbon disulfide and the solution purified beforehand in this manner is added to an aqueous formaldehyde solution.

Since the reactions are isothermic but both the intermediate and the active ingredient are thermally unstable, it is advisable to reduce the reaction temperature by cooling.

In general, the reactions take place at a sufficient rate at above 10° C. At above 50° C., there is already marked formation of undesirable decomposition products. For this reason, the reactions are usually carried out at from 10° to 40° C., preferably from 15° to 30° C.

While the starting materials II and III are reacted with one another as far as possible in stoichiometric amounts in the one-stage reaction, in general an excess of carbon disulfide (III) is used in the synthesis in two stages.

Regardless of the reaction, formaldehyde is usually likewise used in a slight excess based on the amount of methylamine (II).

With regard to the use according to the invention, suitable diaminoalkylene compounds of the formula VI are those in which $R^1$ and $R^2$ independently of one another are each hydrogen or $C_1$–$C_4$-alkyl, such as methyl, ethyl, propyl, 1-methylethyl, butyl, 1-methylpropyl, 2-methylpropyl or 1,1-dimethylethyl, preferably hydrogen, methyl or ethyl, in particular hydrogen or methyl, and A is a 1,2-ethylene, 1,3-propylene or 1,4-butylene bridge, and these bridges may carry from one to four $C_1$–$C_4$-alkyl groups as stated above, preferably one or two methyl groups.

Preferred diaminoalkylene compounds of the formula VI are 1,2-diaminoethylene, 1-(N-methylamino)-2-aminoethylene, 1,2-di-(N-methylamino)-ethylene, 1,2-diaminopropylene, 1-(N-methylamino)-2-aminopropylene, 1,2-di-(N-methylamino)-propylene, 1,3-diaminopropylene, 1-(N-methylamino)-3-aminopropylene, 1,3-di-(N-methylamino)-propylene, 1,2-diaminobutylene, 1-(N-methylamino)-2-aminobutylene, 1,2-di-(N-methylamino)-butylene, 2,3-diaminobutylene, 2-(N-methylamino)-3-aminobutylene, 2,3-di-(N-methylamino)butylene, 1,4-diaminobutylene, 1-(N-methylamino)-4-aminobutylene and 1,4-(N-methylamino)-butylene.

The use of 1,2-diaminoethylene, 1-(N-methylamino)-2-aminoethylene, 1,2-di-(N-methylamino)-ethylene, 1,2-diaminopropylene, 1,2-di-(N-methylamino)-propylene and 1-(N-methylamino)-2-aminopropylene is particularly preferred, and both the pure compounds and mixtures of these compounds may be used.

Usually from 0.1 to 10, preferably from 0.2 to 5, in particular from 0.5 to 1.5, mol %, based on the amount of methylamine (II) used, of diaminoalkylene VI are added to the reaction mixture.

By also adding seed crystals, it is furthermore possible in this process to influence the size of the granules in a conventional manner. For example, small granules would be expected in the case of a very high content, based on the starting materials, of seed crystals, whereas a very low content of seed crystals would result in larger granules.

Finely divided tetrahydro-3,5-dimethyl-1,3,5-thiadiazine-2-thione (I) is used as seed crystals in an amount from 1.5 to 10, preferably from 2.5 to 7.5, in particular from 3 to 6, mol %, based on V, seed crystals having a particle size (diameter) of less than 100 μm being employed. Usually, about 90% of the particles should have sizes of from 50 to 5 μm. A particle size distribution in which 100% of the particles are smaller than 100 μm, about 90% are from 50 to 5 μm and about 10% are smaller than 5 μm is particularly preferred.

In order to achieve a very uniform distribution in the reaction medium from the beginning of the addition of seed crystals, the latter are added to the reaction medium preferably in the form of an aqueous suspension.

The suspension of the seed crystals is mixed with the aqueous formaldehyde solution, both in the one-stage reaction and in the reaction in two stages.

The size of the granules obtainable by the novel process can be influenced not only by the addition of the seed crystals and the amount of diaminoalkylene VI but also by the rate of addition of the reactants (formaldehyde solution in the one-stage reaction or carbamate solution in the reaction in two stages), by the intensity of mixing of the reactants during the reaction and by the duration of mixing of the reactants after the end of the addition of formaldehyde solution in the one-stage reaction or of carbamate solution in the reaction in two stages, where these parameters must be determined on the basis of general technical knowledge, owing to their dependence on the amount of reactants, the dependence on the geometry of the reaction vessel and the dependence on the method of mixing. The following generally known relationships should be noted here: The higher the rate of addition of the reactants, the smaller are the granules formed. The more intense the mixing of the reactants, the smaller are the granules formed, and in addition abrasion effects may result in the product having a high content of very fine material (fine fraction), which may lead to product dust after drying. The longer mixing is continued after the end of the addition, the more pronounced are abrasion effects and hence the larger is the fine fraction in the product.

The granules obtainable by the process of the invention are suitable for soil decontamination in the manner known per se for the active ingredient.

Process Examples

EXAMPLE 1

140.5 g of carbon disulfide was added to a mixture of 111 g of methylamine, 4.37 g of ethylenediamine, 1.24 g of N-methylethylenediamine and 520 ml of water while stirring at from 20° to 30° C. After the end of the addition, the reaction mixture was stirred for 2 hours at 5° C. and then made up to a volume of 800 ml with water.

The solution thus obtained was then added at from 30° to 50° C. to a prepared mixture of 410 g of a 30% strength formaldehyde solution and 400 ml of water.

The resulting tetrahydro-3,5-dimethyl-1,3,5-thiadiazine-2-thione granules were separated off from the mother liquor, washed and dried. 80% of the resulting granules had a diameter of 400 to 500 μm.

EXAMPLE 2

Dithiocarbamate solution was first prepared, by a procedure similar to that in Example 1, at from 30° to 50° C., from 293.7 g of a 40% strength methylamine solution (in water, corresponding to 117.5 g of methylamine) and 2.25 g of ethylenediamine in 300 ml of water by adding 157.8 g of carbon disulfide. After unreacted carbon disulfide has been separated off, the mixture was made up to a volume of 800 ml with water.

By adding the solution thus obtained to a mixture of 322 g of 40% strength aqueous formaldehyde solution which contains 15 g of seed crystals (particle size distribution: 100% by weight smaller than 100 μm, about 90% by weight from 50 to 5 μm and about 10% by weight smaller than 5 μm) and 900 ml of water, tetrahydro-3,5-dimethyl-1,3,5-thiadiazine-2-thione granules were obtained (after isolation, purification and drying) where 100% by weight of the granules had a diameter smaller than 400 μm, about 90% by weight of the particles had a diameter of from 400 to 100 μm and less than 10% by weight had a diameter smaller than 100 μm.

We claim:

1. A process for the preparation of substantially dust-free granules of tetrahydro-3,5-dimethyl-1,3,5-thiadiazine-2-thione (I) of the formula

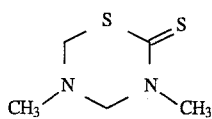

wherein said granules contain dimers or higher polymers of the active ingredient, in which two nitrogen atoms of the dimers or higher polymers not belonging to the same molecule I are linked to one another by a 1,2-ethylene, 1,3-propylene or 1,4-butylene bridge, which process comprises: reacting methylamine (II) and from 0.1 to 10 mol %, based on (II) of at least one diaminoalkylene of the formula VI $$R^1\text{-NH-A-NH-}R^2 \qquad \text{VI}$$

where $R^1$ and $R^2$ independently of one another are each hydrogen or $C_1$–$C_4$-alkyl and A is a 1,2-ethylene, 1,3-propylene or 1,4-butylene bridge, and these bridges may carry from one to four $C_1$–$C_4$-alkyl groups, with carbon disulfide (III) and formaldehyde (IV).

2. A process as defined in claim 1, wherein in a first stage methylamine (II) and of from 0.1 to 10 mol %, based on (II) of at least one diaminoalkylene (VI) are reacted with carbon disulfide (II) to form the corresponding ammonium salts of the dithiocarbamic acid derivatives based on II and VI and the resulting ammonium salts of the dithiocarbamic acid derivatives are reacted with formaldehyde.

3. A process as defined in claim 1, wherein the reaction is carried out in the presence of finely divided tetrahydro-3,5-dimethyl-1,3,5-thiadiazine-2-thione (I).

4. A process as defined in claim 1, wherein in the diaminoalkylene of the formula VI, $R^1$ or $R^2$ independently of one another are hydrogen, methyl or ethyl and A is an ethylene bridge which in turn may carry one to two methyl or ethyl groups.

5. A process as defined in claim 3, wherein the finely divided tetrahydro-3,5-dimethyl-1, 3,5-thiadiazine-2-thione (I) is used in an amount from 1.5 to 10 mol %, based on the methylammonium salt of N-methyldithiocarbamic acid (V).

6. A process as defined in claim 3, wherein the finely divided tetrahydro-3,5-dimethyl-1,3,5-thiadiazine-2-thione (I) has a particle size of less than 100 μm.

7. A process as defined in claim 3, wherein the finely divided tetrahydro-3,5-dimethyl-1,3,5-thiadiazine-2-thione (I) is used in the form of an aqueous suspension.

8. Substantially dust-free granules of tetrahydro-3,5-dimethyl-1,3,5-thiadiazine-2-thione, obtained by the process of claim 7, wherein said granules contain dimers or higher polymers of the active ingredient, in which dimers or higher polymers two nitrogen atoms not belonging to the same molecule I are linked to one another by a 1,2-ethylene, 1,3-propylene or 1,4-butylene bridge corresponding to substituent A.

9. A method of soil decontamination, which comprises treating the soil with an effective amount of substantially dust-free granules of tetrahydro-3,5-dimethyl-1,3,5-thiadiazine-2-thione as defined in claim 8.

10. A method of controlling nematodes, germinating plants and soil fungi, which comprises treating the earth with an effective amount of substantially dust-free granules of tetrahydro-3,5-dimethyl-1,3,5-thiadiazine-2-thione as defined in claim 8.

* * * * *